United States Patent
Schmidt et al.

(10) Patent No.: US 6,887,533 B2
(45) Date of Patent: May 3, 2005

(54) FLUORINATED OXAANTHRACENES AND THEIR USE IN LIQUID-CRYSTAL MIXTURES

(75) Inventors: Wolfgang Schmidt, Dreieich (DE); Barbara Hornung, Hasselroth (DE); Rainer Wingen, Hofheim (DE)

(73) Assignee: Clariant International, Ltd., Muttenz (CH)

( * ) Notice: Subject to any disclaimer, the term of this patent is extended or adjusted under 35 U.S.C. 154(b) by 0 days.

(21) Appl. No.: 10/808,147

(22) Filed: Mar. 24, 2004

(65) Prior Publication Data

US 2004/0245498 A1 Dec. 9, 2004

(30) Foreign Application Priority Data

Mar. 27, 2003 (DE) .......................... 103 13 700

(51) Int. Cl.[7] .................. C09K 19/34; C09K 19/32; C07D 311/82; C07D 311/92; C07C 25/22
(52) U.S. Cl. ............. 428/1.1; 252/299.61; 252/299.62; 549/385; 549/388; 549/389; 570/183; 570/187
(58) Field of Search ..................... 252/299.61, 299.62; 428/1.1; 549/385, 388, 389; 570/183, 187

(56) References Cited

U.S. PATENT DOCUMENTS

| 6,558,758 B1 | 5/2003 | Yanai et al. |
| 6,682,785 B2 | 1/2004 | Wingen et al. |

FOREIGN PATENT DOCUMENTS

| DE | 100 50 071 A1 | 6/2001 |
| DE | 101 45 778 A1 | 4/2003 |

OTHER PUBLICATIONS

H. Ichinose et al., "High Optical Anisotropy and Small Rotational Viscosity LC Mixture for Field–Sequential Color TN–LCDs", Seventh International Display Workshop, Nov. 29–Dec. 1, 2000, Kobe Japan.

Primary Examiner—Shean C. Wu
(74) Attorney, Agent, or Firm—Frommer Lawrence & Haug LLP

(57) ABSTRACT

Compounds of the formula (I)

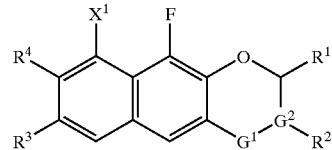

(I)

where:
  $X^1$ is H or F
  $G^1$-$G^2$ is —$CH_2$—CH— or CH=C—
  $R^1$, $R^2$ are
  a) H
  b) the $M^2$-$A^2$-$R^5$ moiety
  c) for example, a straight-chain or branched alkyl radical having from 1 to 16 carbon atoms
  $R^3$ and $R^4$ are each, for example, H, the $M^2$-$A^2$-$R^5$ moiety or a straight-chain or branched alkyl or alkyloxy radical having from 1 to 16 carbon atoms
  $A^2$ is, for example, 1,4-phenylene,
with the provisos that
  a) when $R^2$ is not H, $R^1$ and $R^3$ have to be H,
  b) when $R^2$ is H, $R^4$ must not have the definitions c) or d),
  c) $R^1$, $R^2$, $R^3$ and $R^4$ must not at the same time be H.

9 Claims, 1 Drawing Sheet

FLUORINATED OXAANTHRACENES AND THEIR USE IN LIQUID-CRYSTAL MIXTURES

An ever-increasing number of applications of LCDs, for example for use in cars, in which a temperature range of from −40° C. to 100° C. can quite possibly exist, but also for transportable units such as cell phones and notebook PCs, requires liquid-crystal mixtures which have firstly a very wide working temperature range and secondly a very low threshold voltage.

There is therefore a continuing demand for novel, suitable liquid-crystal mixtures and mixture components. As described in Ichinose et al. (IDW'00, Abstr. LCT4-3) or in DE-A 10050071, materials are sought in which there is coexistence of high optical anisotropy (Δn) and low rotational viscosity, although other parameters, for example high absolute values of dielectric anisotropy (Δ∈) are likewise required, in addition to further parameters relevant to the application.

It is therefore an object of the present invention to provide novel components for use in nematic or cholesteric or chiral-smectic liquid-crystal mixtures which have high absolute values of dielectric anisotropy combined with a favorable ratio of viscosity to clearing point. In addition, the compounds should to a high degree be light- and UV-stable, and also thermally stable. In addition, they should be suitable for realizing high voltage holding ratio (VHR). In addition, they should have good synthetic accessibility and therefore potentially be inexpensive.

DE-101 45 778.2 discloses fluorinated anthracenes for use in liquid-crystal mixtures. However, since the manufacturers of liquid-crystal displays have an interest in continually improved liquid-crystal mixtures, there is a need for further components of liquid-crystal mixtures, with which individual parameters relevant to the application can be optimized.

Figure 1:
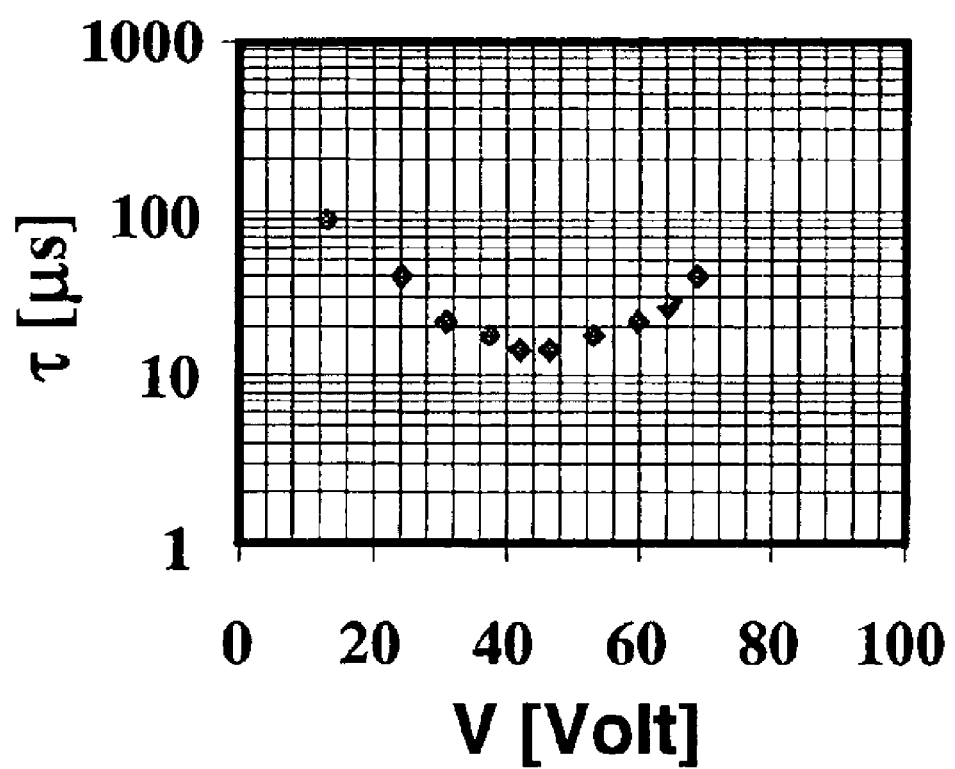
FIG. 1 shows the τVmin curve (τ plotted against the voltage) at Tc=30K.

The present invention therefore provides compounds of the formula (I) and also liquid-crystal mixtures comprising these compounds

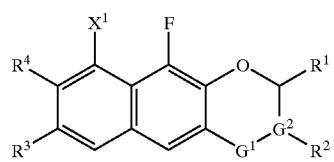

(I)

where:
X$^1$ is H or F
G$^1$-G$^2$ is —CH$_2$—CH— or CH═C—
R$^1$, R$^2$ are
a) H
b) the M$^2$-A$^2$-R$^5$ moiety
c) a straight-chain or branched alkyl radical having from 1 to 16 carbon atoms or a straight-chain or branched alkenyl radical having from 2 to 16 carbon atoms, in each of which
  c1) one or more nonadjacent and nonterminal CH$_2$ groups may be replaced by —O—, —C(═O)O—, —O—C(═O)—, —O—C(═O)—O—, —C(═O)— or —Si(CH$_3$)$_2$— and/or
  c2) one CH$_2$ group may be replaced by —C≡C—, cyclopropane-1,2-diyl, cyclobutane-1,3-diyl, cyclohexane-1,4-diyl or phenylene-1,4-diyl and/or
  c3) one or more hydrogen atoms may be replaced by F and/or Cl, R$^3$ is
a) H
b) the M$^2$-A$^2$-R$^5$ moiety
c) a straight-chain or branched alkyl or alkyloxy radical having from 1 to 16 carbon atoms or a straight-chain or branched alkenyl or alkenyloxy radical having from 2 to 16 carbon atoms, in each of which
  c1) one or more nonadjacent and nonterminal CH$_2$ groups may be replaced by —O—, —C(═O)O—, —O—C(═O)—, —O—C(═O)—O—, —C(═O)— or —Si(CH$_3$)$_2$— and/or
  c2) one CH$_2$ group may be replaced by —C≡C—, cyclopropane-1,2-diyl, cyclobutane-1,3-diyl, cyclohexane-1,4-diyl or phenylene-1,4-diyl and/or
  c3) one or more hydrogen atoms may be replaced by F and/or Cl, R$^4$ is
a) H
b) F, Cl, CN, —NCS, CF$_3$, CHF$_2$, CH$_2$F, OCF$_3$, OCHF$_2$, OCH$_2$F, OCH$_2$CF$_3$, OCH═CF$_2$
c) the M$^2$-A$^2$-R$^5$ moiety
d) a straight-chain or branched alkyl or alkyloxy radical having from 1 to 12 carbon atoms or a straight-chain or branched alkenyl or alkenyloxy radical having from 2 to 12 carbon atoms, in each of which
  d1) one or more nonadjacent and nonterminal CH$_2$ groups may be replaced by —O—, —C(═O)O—, —O—C(═O)—, —O—C(═O)—O—, —C(═O)— or —Si(CH$_3$)$_2$— and/or
  d2) one CH$_2$ group may be replaced by —C≡C—, cyclopropane-1,2-diyl or cyclobutane-1,3-diyl and/or
  d3) one or more hydrogen atoms may be replaced by F and/or Cl, M$^2$ is —CO—O—, —O—CO—, —CH$_2$—O—, —O—CH$_2$—, —CF$_2$—O—, —O—CF$_2$—, —CH═CH—, —CF═CF—, —C≡C—, —CH$_2$—CH$_2$—CO—O—, —O—CO—CH$_2$—CH$_2$—, —CH$_2$—CH$_2$—, —CF$_2$—CF$_2$—, —(CH$_2$)$_4$—, —OC(═O)CF═CF— or a single bond A$^2$ is 1,4-phenylene in which one or two hydrogen atoms may be replaced by F, Cl, CN and/or OCF$_3$ or up to three hydrogen atoms may be replaced by fluorine, is 1,4-cyclohexylene in which one or two hydrogen atoms may be replaced by CH$_3$ and/or F, is 1-cyclohexene-1,4-diyl in which one hydrogen atom may be replaced by CH$_3$ or F or is 1,3-dioxane-2,5-diyl, R$^5$ has the same possible definitions as R$^3$ except -M$^2$-A$^2$-R$^5$, with the provisos that
a) when R$^2$ is not H, R$^1$ and R$^3$ each have to be H,
b) when R$^2$ is H, R$^4$ must not have the definitions c) or d),
c) R$^1$, R$^2$, R$^3$ and R$^4$ must not at the same time be H.

Preference is given to the compounds of the formulae (Ia) to (Ik):

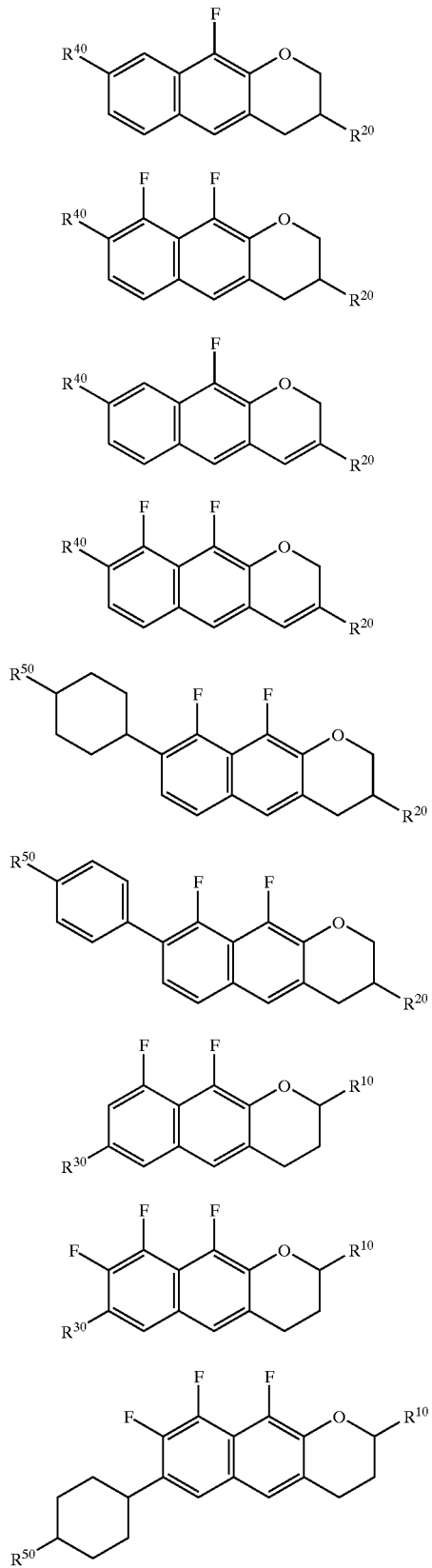

(Ia)
(Ib)
(Ic)
(Id)
(Ie)
(If)
(Ig)
(Ih)
(Ii)

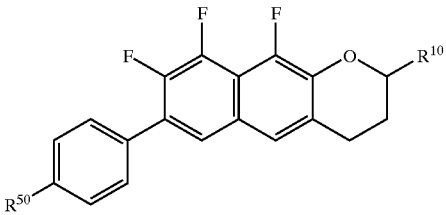

(Ik)

In these structures:

$R^{10}$ is H or a straight-chain or branched alkyl radical having from 1 to 6 carbon atoms or a straight-chain or branched alkenyl radical having from 2 to 6 carbon atoms, in each of which one (nonterminal or adjacent to the ring) —CH$_2$ group may also be replaced by —O—

$R^{20}$ is H or a straight-chain or branched alkyl radical having from 1 to 6 carbon atoms or a straight-chain or branched alkenyl radical having from 2 to 6 carbon atoms, in each of which one (nonterminal or adjacent to the ring) —CH$_2$ group may also be replaced by —O—

$R^{30}$ is H or a straight-chain or branched alkyl radical having from 1 to 6 carbon atoms or a straight-chain or branched alkenyl radical having from 2 to 6 carbon atoms, in each of which one (nonterminal or adjacent to the ring) —CH$_2$ group may also be replaced by —O—

$R^{40}$ is H or a straight-chain or branched alkyl radical having from 1 to 6 carbon atoms or a straight-chain or branched alkenyl radical having from 2 to 6 carbon atoms, in each of which one (nonterminal or adjacent to the ring) —CH$_2$ group may also be replaced by —O—

$R^{50}$ is H or a straight-chain or branched alkyl radical having from 1 to 6 carbon atoms or a straight-chain or branched alkenyl radical having from 2 to 6 carbon atoms.

The provision of compounds of the formula (I) in a quite general sense considerably broadens the range of liquid-crystalline substances which are suitable for producing liquid-crystalline mixtures from different performance aspects.

In this context, the compounds of the formula (I) have a broad field of application. Depending on the selection of the substituents, they may be added to other classes of compound, in order, for example, to influence the dielectric and/or optical anisotropy of such a dielectric. They may also serve to optimize its threshold voltage and/or its viscosity. The compounds may also serve to increase the mesophase range or to adapt individual mesophases to parameters relevant to the application.

The compounds of the formula (I) are particularly suitable for influencing dielectric anisotropy ($\Delta\in$) even in small amounts in the mixture.

The compounds of the formula (I) are particularly suitable for reducing the switching time of ferroelectric liquid-crystal mixtures, even in small amounts in the mixture.

The compounds of the formula (I) are likewise particularly suitable for adjusting the broadness of the $S_C$ or N phase to application requirements.

The present invention thus provides compounds of the formula (I) and also the use of these compounds as components of liquid-crystalline mixtures and liquid-crystalline mixtures comprising compounds of the formula (I).

The compounds of the formula (I) may be used in various liquid-crystal mixtures. In the case of nematic mixtures, they are particularly suitable for active matrix displays (AM- LCD) (see, for example, C. Prince, Seminar Lecture Notes, Volume I, p. M-3/3–M-22, SID International Symposium 1997, B. B: Bahadur, Liquid Crystal Applications and Uses, Vol. 1, p. 410, World Scientific Publishing, 1990, E. Lüder, Recent Progress of AMLCD's, Proceedings of the 15$^{th}$ International Display Research Conference, 1995, p. 9–12) and in-plane-switching displays (IPS-LCD), and, in the case of smectic liquid-crystal mixtures, for suitably smectic (ferroelectric or antiferroelectric) displays.

Further components of liquid-crystal mixtures which comprise inventive compounds of the formula (I) are preferably selected from the known compounds having smectic and/or nematic and/or cholesteric phases. Mixture components suitable in this context are listed in particular in WO 00/36054, DE-A-19 531 165 and EP-A-0 893 424, which are explicitly incorporated herein by way of reference.

The present invention therefore also provides liquid-crystal mixtures, which comprise at least one compound of the formula (I), preferably in an amount of from 1 to 40% by weight, based on the liquid-crystal mixture. The mixtures preferably comprise at least 3 further components. The invention additionally provides electrooptical displays which comprise the mixtures according to the invention.

Preference is given to displays which comprise the inventive nematic or smectic (ferroelectric or antiferroelectric) mixtures in combination with active matrix elements.

The displays according to the invention are typically constructed in such a way that a liquid crystal layer is enclosed on both sides by layers which are typically, in this sequence starting from the LC layer, at least one alignment layer, electrodes and a boundary layer (for example of glass). In addition, they may comprise spacers, adhesive frames, polarizers and thin color filter layers for color displays. Further possible components are antireflection, passivation, compensation and barrier layers, and also electrically nonlinear elements such as thin-film transistors (TFT) and metal-insulator-metal (MIM) elements. The construction of liquid-crystal displays has already been described in detail in relevant monographs (see, for example, E. Kaneko, "Liquid Crystal TV Displays: Principles and Applications of Liquid Crystal Displays", KTK Scientific Publishers, 1987).

Examples of possible synthetic routes to compounds of the formula (I) are specified in the schemes 1 and 2 which follow, although other processes are also feasible and possible.

The following abbreviations are used:

| | |
|---|---|
| n-BuLi | n-butyllithium |
| DCC | dicyclohexylcarbodiimide |
| DDQ | 2,3-dichloro-5,6-dicyano-p-benzoquinone |
| DEAD | diethyl azodicarboxylate (azodicarboxylic acid diethyl ester) |
| Diglyme | diethylene glycol dimethyl ether |
| DMAP | 4-(dimethylamino)pyridine |
| DME | dimethoxyethane |
| DMF | N,N-dimethylformamide |
| KOtBu | potassium tert-butoxide |
| LICOR | lithium organyl + potassium tert-butoxide |
| LiTMP | lithium 2,2,6,6-tetramethylpiperidide |
| MTBE | tert-butyl methyl ether |
| NMP | N-methylpyrrolidone |
| 4-TsOH | 4-toluenesulfonic acid |

The reactants (E1) and (E2) required for the synthesis of (I) by scheme 1 or 2 are commercially available or known from the literature:

$X^1$=H 1-fluoronaphthalene [321-38-0] commercially available $X^1$=F 1,8-difluoronaphthalene [30389-93-6] J.Am..Chem.Soc. 89, 386 (1967)

$X^1$=H, $R^3$=Br 5-fluoro-2-bromonaphthalene [13772-91-3] J.Am.Chem.Soc. 89, 386 (1967)

$X^1$=H, $R^3$=CH$_3$ 7-methyl-1-fluoronaphthalene [70631-71-9] J.Am.Chem.Soc. 89, 386 (1967)

$X^1$=H, $R^3$=CHO 5-fluoronaphthalene-2-carbaldehyde [70631-81-1] J.Am.Chem.Soc. 89, 386 (1967)

$X^1$=F, $R^3$=CHO 4,5-difluoronaphthalene-2-carbaldehyde can be prepared in a similar manner to J. Am. Chem.Soc. 89, 386 (1967).

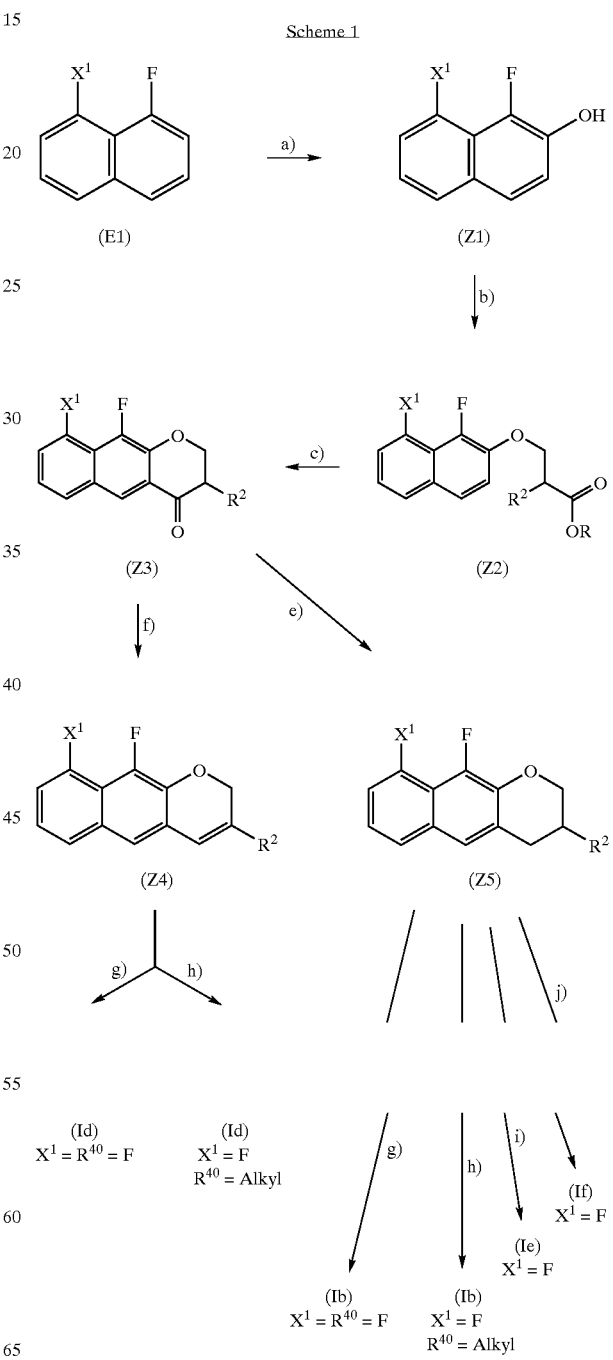

Scheme 1

Scheme 2

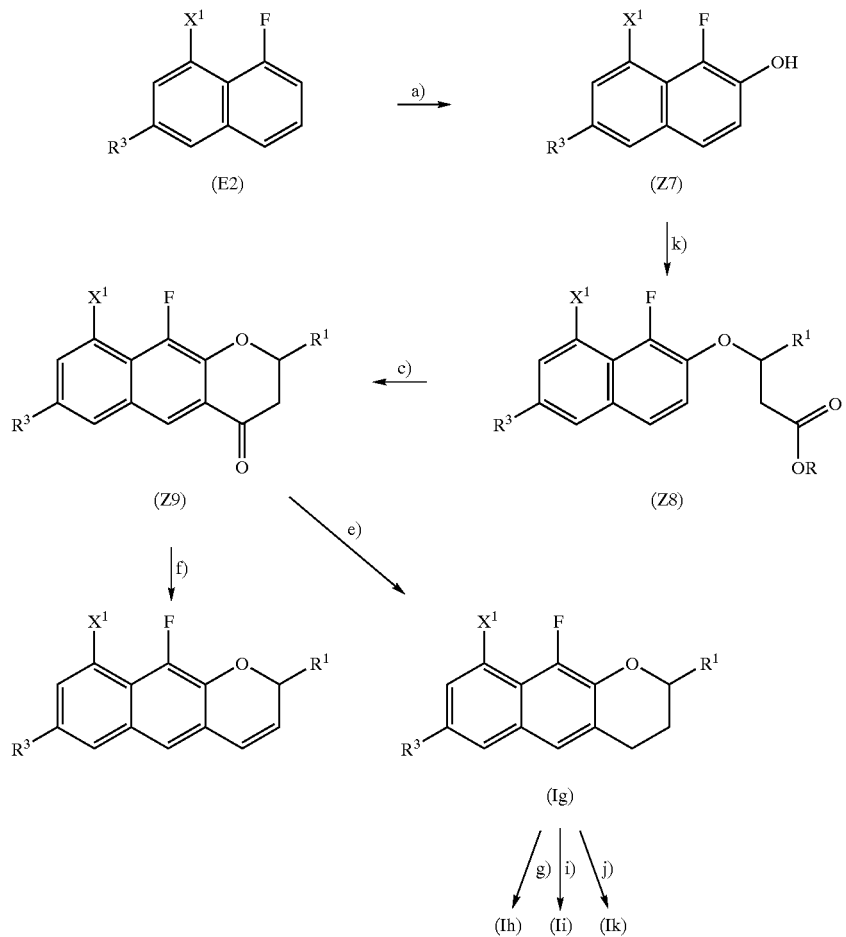

1. LDA 2. B(OCH$_3$)$_3$ 3. H$_2$O$_2$ according to *Synlett* 1990, 747
b) BrCH$_2$CH(R$^2$)CO$_2$R/NaH/DMF according to Larock, *Comprehensive Organic Transformations*, VCH Verlag, Weinheim 1989, ISBN 3-527-26953-3
c) 1. OH— 2. H$^+$ 3. polyphosphoric acid according to *J. Med. Chem* 32, 757 (1989)
e) Et$_3$SiH, trifluoroacetic acid according to DE-A 19840447
f) 1. NaBH$_4$ 2. H$^+$ according to Larock, *Comprehensive Organic Transformations*, VCH Verlag, Weinheim 1989, ISBN 3-527-26953-3
g) 1. LDA 2. NFSi according to *Tetrahedron Letters* 35, 3465 (1994)
h) 1. LDA 2. R$^{40}$ halide according to *Synlett* 1990, 447
i) 1. LDA 2. R$^{50}$-cyclohexanone 3. H$^+$ 4. H$_2$, Pd(C), toluene according to WO 96/00710
j) 1. LDA 2. I$_2$ 3. R$^{50}$-phenylB(OH)$_2$, Pd catalyst according to *J. Chem. Soc. Perkin Trans II* 1989, 2041.
k) R$^1$CHBrCH$_2$CO$_2$R/NaH/DMF according to Larock, *Comprehensive Organic Transformations*, VCH Verlag, Weinheim 1989, ISBN 3-527-26953-3

The invention is illustrated in detail by the examples which follow.

EXAMPLE 1

8,9-Difluoro-3-methyl-7-propyl-1,2,3,4-tetrahydro-1-oxaanthracene [(Ib) where R$^{20}$=CH$_3$, R$^{40}$=C$_3$H$_7$)]

a) A solution, cooled to −70° C., of 20 mmol of diisopropylamine in 20 ml of tetrahydrofuran was admixed with 21 mmol of n-butyllithium (1.6 M solution in n-hexane). After 30 min, a solution of 20 mmol of 1,8-difluoronaphthalene [30389-93-6], obtained by Baltz-Schiemann reaction from commercially available 1,8-diaminonaphthalene according to J.Am.Chem.Soc. 89, 386 (1967), was added dropwise and the mixture was stirred for a further 4 h. At the same temperature, 21 mmol of trimethyl borate were added dropwise and the mixture was brought to room temperature overnight with stirring. A mixture of 12 ml of water and 4 ml of hydrochloric acid (conc.) was then added, and also, after stirring for a further half hour, 100 ml of tert-butyl methyl ether. The organic phase was removed and washed with water.

b) This solution of crude 1,8-difluoronaphthalene-2-boronic acid was then heated to 55° C. and 6 ml of hydrogen peroxide (35 percent aqueous solution) were added dropwise. After the end of the reaction, the mixture was cooled to 0° C. and excess hydrogen peroxide was destroyed by adding aqueous sodium sulfite solution. The organic phase was washed with water and dried, and the solvent was removed under reduced pressure.

c) The crude 1,8-difluoro-2-naphthol was dissolved in 25 ml of dimethylformamide and 23 mmol of sodium hydride were added. After the end of the development of hydrogen, 30 mmol of methyl 3-bromoisobutyrate [59154-46-0] (commercially available) were added and the mixture was stirred at room temperature. After the end of the reaction, the mixture was added to a mixture of 250 ml of water and 100 ml of dichloromethane, and the organic phase was removed, dried and concentrated by rotary evaporation. The mixture was filtered through 100 g of silica gel using toluene and the filtrate was concentrated by rotary evaporation. Heating with 20 ml of 10% sodium hydroxide solution in 100 ml of tetrahydrofuran, admixing with semiconcentrated hydrochloric acid and removing water and tetrahydrofuran provided 3.5 g of crude 3-(1,2-difluoronaphthalene-2-yl)-oxy-2-methylpropionic acid of honeylike consistency.

d) This was admixed with 50 g of polyphosphoric acid and heated to 100° C. with stirring. After the end of the reaction, the mixture was poured onto ten times the amount of water and extracted with dichloromethane. The extract was washed with water, briefly dried over sodium sulfate and filtered through 100 g of silica gel. After the solvent had been distilled off, 2.1 g of 8,9-difluoro-3-methyl-4-oxo-1,2,3,4-tetra-hydro-1-oxaanthracene were obtained.

e) This was dissolved in 50 ml of trifluoroacetic acid, 3 g of triethylsilane were slowly metered in and the mixture was stirred until the end of the reaction, finally with heating to 50° C. After cooling, the mixture was added to 500 ml of water, extraction was effected with dichloromethane, and the extract was washed with water and subsequently 10% sodium hydrogencarbonate solution. After drying over sodium sulfate, the dichloromethane was distilled off, and the residue was taken up in toluene and filtered through 100 g of silica gel.

f) The 8,9-difluoro-3-methyl-1,2,3,4-tetrahydro-1-oxaanthracene (1.5 g) obtained in this way was dissolved in 40 ml of tetrahydrofuran and admixed at −75° C. with 7 mmol of n-butyllithium. After stirring for a further 30 minutes, a solution of 7 mmol of potassium tert-butoxide in 20 ml of tetrahydrofuran was added dropwise. After cooling to −95° C., 15 mmol of propyl bromide were added dropwise. After 2 h, the temperature was cooled to −70° C., the mixture was stirred at this temperature for a further 1 h and was then allowed to come to 0° C. overnight. The mixture was added to 200 ml of ice-water and extracted twice with 100 ml each time of tert-butyl methyl ether, and the organic phases were combined, washed with water and saturated sodium chloride solution and dried. The solvent was distilled off under reduced pressure and the brown residue was chromatographed through 500 g of silica gel using heptane/toluene (9:1, v/v). 0.42 g of 8,9-difluoro-3-methyl-7-propyl-1,2,3,4-tetrahydro-1-oxaanthracene was obtained as a colorless syrup.

EXAMPLE 2

8,9-Difluoro-3-methyl-7-pentyl-1,2-dihydro-1-oxaanthracene [(Id) where $R^{20}=CH_3$, $R^{40}=C_5H_{11}$)]

a) 3.1 g of stage d) of example 1 were added at room temperature to a mixture of 5 mmol of sodium borohydride and 25 ml of 2-propanol. On completion of reaction, the mixture was hydrolyzed and extracted with tert-butyl methyl ether, the extract was washed with water and the solvent distilled off. After 50 ml of toluene and 50 mg of 4-toluenesulfonic acid had been added, the mixture was heated to boiling, and the condensate was conducted through a layer of blue gel to remove water of reaction. On completion of reaction, the mixture was concentrated by evaporation to one third of the original volume and filtered through 100 g of silica gel. After the solvent had been distilled off, 2.2 g of 8,9-difluoro-3-methyl-1,2-dihydro-1-oxaanthracene were obtained as a yellowish oil.

b) This was reacted with pentyl bromide under the conditions of stage 1 of example 1. After further treatment as in the case specified, 1.4 g of 8,9-difluoro-3-methyl-7-pentyl-1,2-dihydro-1-oxaanthracene were obtained as a colorless syrup.

EXAMPLE 3

A chiral-smectic C mixture consisting of

| | |
|---|---|
| 2-(4-heptyloxyphenyl)-5-nonylpyrimidine | 19.6% |
| 5-nonyl-2-(4-octyloxyphenyl)pyrimidine | 19.6% |
| 5-nonyl-2-(4-nonyloxyphenyl)pyrimidine | 19.6% |
| 2-(2,3-difluoro-4-heptyloxyphenyl)-5-nonylpyrimidine | 6.5% |
| 2-(2,3-difluoro-4-octyloxyphenyl)-5-nonylpyrimidine | 6.5% |
| 2-(2,3-difluoro-4-nonyloxyphenyl)-5-nonylpyrimidine | 6.5% |
| 5-hexyloxy-2-(4-hexyloxyphenyl)pyrimidine | 19.6% |
| (S)-4-[4'-(2-fluorooctyloxy)biphenyl-4-yl]-1-heptylcyclohexanecarbonitrile | 2.0% | is admixed with 5% of the compound of example 2.

This results in a mixture which, as shown in FIG. 1, is suitable for the operation of displays in inverse mode, since the curve has the required minimum and the values are within the technically relevant range.

FIG. 1 shows the τVmin curve (τ plotted against the voltage) at $T_C$−30K, monopolar pulses and a cell separation of 1.3 μm.

EXAMPLE 4

A nematic mixture consisting of

| | |
|---|---|
| 4-[(1E)-1-propenyl]-4'-propyl-1,1'-bicyclohexyl | 3.0% |
| 4-[(4-ethenyl)-1,1'-bicyclohexyl-4'-yl]methylbenzene | 5.0% |
| compound from example 1 | 5.0% |
| 1-ethoxy-2,3-difluoro-4-[4-ethyl-1,1'-bicyclohexyl-4'-yl]benzene | 6.0% |
| 1-ethoxy-2,3-difluoro-4-[4-propyl-1,1'-bicyclohexyl-4'-yl]benzene | 6.0% |
| 1-ethoxy-2,3-difluoro-4-[4-pentyl-1,1'-bicyclohexyl-4'-yl]benzene | 6.0% |
| 1-methyl-2,3-difluoro-4-[4-ethyl-1,1'-bicyclohexyl-4'-yl]benzene | 6.0% |
| 4-ethyl-4'-(4-propylcyclohexyl)-1,1'-biphenyl | 8.0% |
| 1-butoxy-2,3-difluoro-4-(4-propylcyclohexyl)benzene | 12.0% |
| 1-ethoxy-2,3-difluoro-4-(4-pentylcyclohexyl)benzene | 12.0% |
| 1-methyl-2,3-difluoro-4-[4-propyl-1,1'-bicyclohexyl-4'-yl]benzene | 14.0% |
| 1-butoxy-2,3-difluoro-4-(4-pentylcyclohexyl)benzene | 15.0% | has the values: clearing point: 81° C., Δ∈ [1 kHz, 20° C.]: −5.1 and $γ_1$ [mPa·s, 20° C.]: 320, all of which are within the technically relevant range.

What is claimed is:

1. Compounds of the formula (I)

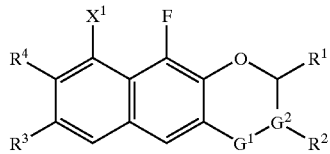

where:

$X^1$ is H or F $G^1$-$G^2$ is —CH$_2$—CH— or CH=C—

$R^1$, $R^2$ are a) H b) the $M^2$-$A^2$-$R^5$ moiety c) a straight-chain or branched alkyl radical having from 1 to 16 carbon atoms or a straight-chain or branched alkenyl radical having from 2 to 16 carbon atoms, in each of which c1) one or more nonadjacent and nonterminal CH$_2$ groups may be replaced by —O—, —C(=O)O—, —O—C(=O)—, —O—C(=O)—O—, —C(=O)— or —Si(CH$_3$)$_2$— and/or c2) one CH$_2$ group may be replaced by —C≡C—, cyclopropane-1,2-diyl, cyclobutane-1,3-diyl, cyclohexane-1,4-diyl or phenylene-1,4-diyl and/or c3) one or more hydrogen atoms may be replaced by F and/or Cl, $R^3$ is a) H b) the $M^2$-$A^2$-$R^5$ moiety c) a straight-chain or branched alkyl or alkyloxy radical having from 1 to 16 carbon atoms or a straight-chain or branched alkenyl or alkenyloxy radical having from 2 to 16 carbon atoms, in each of which c1) one or more nonadjacent and nonterminal CH$_2$ groups may be replaced by —O—, —C(=O)O—, —O—C(=O)—, —O—C(=O)—O—, —C(=O)— or —Si(CH$_3$)$_2$— and/or c2) one CH$_2$ group may be replaced by —C≡C—, cyclopropane-1,2-diyl, cyclobutane-1,3-diyl, cyclohexane-1,4-diyl or phenylene-1,4-diyl and/or c3) one or more hydrogen atoms may be replaced by F and/or Cl, $R^4$ is a) H b) F, Cl, CN, —NCS, CF$_3$, CHF$_2$, CH$_2$F, OCF$_3$, OCHF$_2$, OCH$_2$F, OCH$_2$CF$_3$, OCH=CF$_2$ c) the $M^2$-$A^2$-$R^5$ moiety d) a straight-chain or branched alkyl or alkyloxy radical having from 1 to 12 carbon atoms or a straight-chain or branched alkenyl or alkenyloxy radical having from 2 to 12 carbon atoms, in each of which d1) one or more nonadjacent and nonterminal CH$_2$ groups may be replaced by —O—, —C(=O)O—, —O—C(=O)—, —O—C(=O)—O—, —C(=O)— or —Si(CH$_3$)$_2$— and/or d2) one CH$_2$ group may be replaced by —C≡C—, cyclopropane-1,2-diyl or cyclobutane-1,3-diyl and/or d3) one or more hydrogen atoms may be replaced by F and/or Cl, $M^2$ is —CO—O—, —O—CO—, —CH$_2$—O—, —O—CH$_2$—, —CF$_2$—O—, —O—CF$_2$—, —CH=CH—, —CF=CF—, —C≡C—, —CH$_2$—CH$_2$—CO—O—, —O—CO—CH$_2$—CH$_2$—, —CH$_2$—CH$_2$—, —CF$_2$—CF$_2$—, —(CH$_2$)$_4$—, —OC(=O)CF=CF— or a single bond $A^2$ is 1,4-phenylene in which one or two hydrogen atoms may be replaced by F, Cl, CN and/or OCF$_3$ or up to three hydrogen atoms may be replaced by fluorine, is 1,4-cyclohexylene in which one or two hydrogen atoms may be replaced by CH$_3$ and/or F, is 1-cyclohexene-1,4-diyl in which one hydrogen atom may be replaced by CH$_3$ or F or is 1,3-dioxane-2,5-diyl, $R^5$ has the same possible definitions as $R^3$ except -$M^2$-$A^2$-$R^5$, with the provisos that a) when $R^2$ is not H, $R^1$ and $R^3$ have to be H, b) when $R^2$ is H, $R^4$ must not have the definitions c) or d), c) $R^1$, $R^2$, $R^3$ and $R^4$ must not at the same time be H.

2. Compounds of the formula (I) as claimed in claim 1 corresponding to the partial structures (Ia) to (Ik):

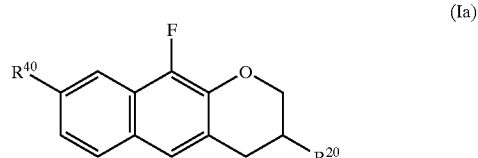

(Ia)

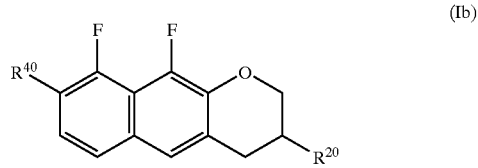

(Ib)

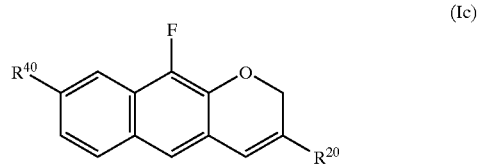

(Ic)

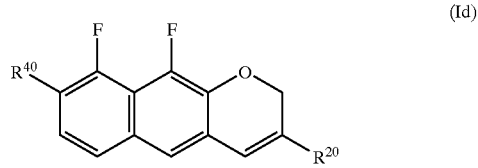

(Id)

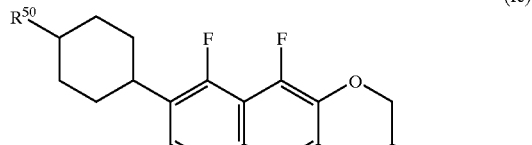

(Ie)

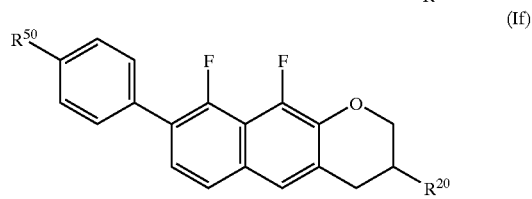

(If)

-continued

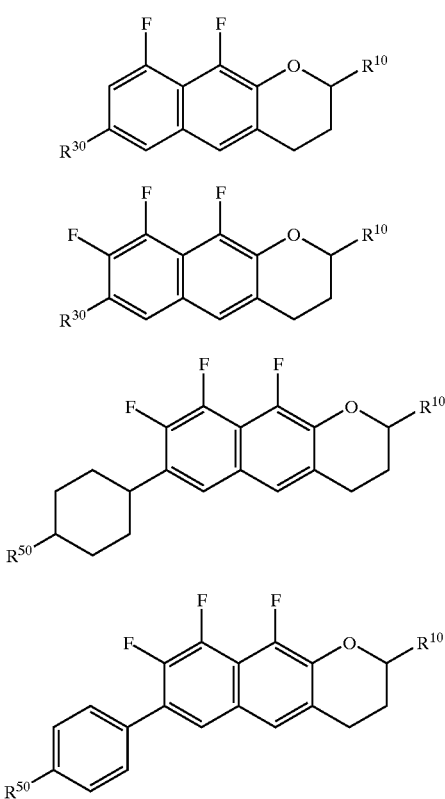

(Ig)

(Ih)

(Ii)

(Ik)

$R^{10}$ is H or a straight-chain or branched alkyl radical having from 1 to 6 carbon atoms or a straight-chain or branched alkenyl radical having from 2 to 6 carbon atoms, in each of which one (nonterminal or adjacent to the ring) —CH$_2$ group may also be replaced by —O—

$R^{20}$ is H or a straight-chain or branched alkyl radical having from 1 to 6 carbon atoms or a straight-chain or branched alkenyl radical having from 2 to 6 carbon atoms, in each of which one (nonterminal or adjacent to the ring) —CH$_2$ group may also be replaced by —O—

$R^{30}$ is H or a straight-chain or branched alkyl radical having from 1 to 6 carbon atoms or a straight-chain or branched alkenyl radical having from 2 to 6 carbon atoms, in each of which one (nonterminal or adjacent to the ring) —CH$_2$ group may also be replaced by —O—

$R^{40}$ is H or a straight-chain or branched alkyl radical having from 1 to 6 carbon atoms or a straight-chain or branched alkenyl radical having from 2 to 6 carbon atoms, in each of which one (nonterminal or adjacent to the ring) —CH$_2$ group may also be replaced by —O—

$R^{50}$ is H or a straight-chain or branched alkyl radical having from 1 to 6 carbon atoms or a straight-chain or branched alkenyl radical having from 2 to 6 carbon atoms.

3. A liquid-crystal mixture comprising at least one compound of the formula (I) as claimed in claim 1.

4. The liquid-crystal mixture as claimed in claim 3, which comprises one or more compounds of the formula (I) in an amount of from 1 to 40% by weight, based on the liquid-crystal mixture.

5. The liquid-crystal mixture as claimed in claim 3, which comprises at least three further components having smectic and/or nematic and/or cholesteric phases.

6. The liquid-crystal mixture as claimed in claim 3, which is chiral-smectic.

7. The liquid-crystal mixture as claimed in claim 3, which is nematic or cholesteric.

8. A liquid-crystal display comprising a liquid-crystal mixture as claimed in claim 3.

9. The liquid-crystal display as claimed in claim 8, which is operated in ECB, IPS or VA display mode and in which the liquid-crystal mixture is nematic or cholesteric.

* * * * *